US012740926B2

(12) United States Patent
Suma et al.

(10) Patent No.: US 12,740,926 B2
(45) Date of Patent: Sep. 22, 2026

(54) SURFACE-MODIFIED ZINC OXIDE PARTICLES, LIQUID DISPERSION, AND COSMETIC

(71) Applicant: SUMITOMO OSAKA CEMENT CO., LTD., Tokyo (JP)

(72) Inventors: Syunsuke Suma, Tokyo (JP); Masahiro Nobe, Tokyo (JP)

(73) Assignee: SUMITOMO OSAKA CEMENT CO., LTD., Tokyo (JP)

( * ) Notice: Subject to any disclaimer, the term of this patent is extended or adjusted under 35 U.S.C. 154(b) by 894 days.

(21) Appl. No.: 17/997,348

(22) PCT Filed: Apr. 30, 2020

(86) PCT No.: PCT/JP2020/018241
§ 371 (c)(1),
(2) Date: Oct. 27, 2022

(87) PCT Pub. No.: WO2021/220453
PCT Pub. Date: Nov. 4, 2021

(65) Prior Publication Data

US 2023/0218488 A1 Jul. 13, 2023

(51) Int. Cl.
*A61K 8/02* (2006.01)
*A61Q 17/04* (2006.01)

(52) U.S. Cl.
CPC ............ *A61K 8/0245* (2013.01); *A61Q 17/04* (2013.01); *A61K 2800/412* (2013.01); *A61K 2800/612* (2013.01); *A61K 2800/651* (2013.01)

(58) Field of Classification Search
None
See application file for complete search history.

(56) References Cited

U.S. PATENT DOCUMENTS

2015/0050496 A1 2/2015 Sueda et al.

FOREIGN PATENT DOCUMENTS

EP 2824073 A1 * 1/2015 ............ C09C 1/043
EP 3305272 A1 4/2018

(Continued)

OTHER PUBLICATIONS

English language translation of WO 2017/130632 A1, Publ. Aug. 3, 2017. (Year: 2017).*

(Continued)

*Primary Examiner* — Dominic Lazaro
(74) *Attorney, Agent, or Firm* — Merchant & Gould P.C.

(57) ABSTRACT

Surface-modified zinc oxide particles which have a silane coupling agent having an alkoxy group on surfaces thereof, in which d50 when measured with a laser diffraction/scattering type particle size distribution-measuring instrument by the following measurement method is 4 μm or less. (Measurement method) 10 g of the surface-modified zinc oxide particles, 88 g of cyclopentasiloxane, and 2 g of polyglyceryl-3 polydimethylsiloxyethyl dimethicone are mixed to obtain a liquid mixture, a dispersion treatment is performed on the obtained liquid mixture at 9,500 rpm for 5 minutes using a homogenizer to obtain a liquid dispersion, the liquid dispersion is diluted with cyclopentasiloxane so that a content of the surface-modified zinc oxide particles in the obtained liquid dispersion is 0.01% by mass to produce a measurement solution, and d50 is measured with the laser diffraction/scattering type particle size distribution-measuring instrument using the obtained measurement solution.

20 Claims, 1 Drawing Sheet

(56) References Cited

FOREIGN PATENT DOCUMENTS

| | | | | | |
|---|---|---|---|---|---|
| EP | 3305272 | B1 * | 4/2022 | ............... | A61K 8/27 |
| JP | 2000-095519 | A | 4/2000 | | |
| JP | 2002-284527 | A | 10/2002 | | |
| JP | 2007-051188 | A | 3/2007 | | |
| JP | 2007-197412 | A | 8/2007 | | |
| JP | 2015-527430 | A | 9/2015 | | |
| WO | 2013-133412 | A | 9/2013 | | |
| WO | 2014/005753 | A1 | 1/2014 | | |
| WO | 2016-190399 | A | 12/2016 | | |
| WO | WO-2016190399 | A1 * | 12/2016 | ............. | A61Q 19/00 |
| WO | 2017/130632 | A | 8/2017 | | |
| WO | WO-2017130632 | A1 * | 8/2017 | ............. | A61Q 17/04 |

OTHER PUBLICATIONS

Opposition issued in Japanese Patent Application No. 2022-518532/ Patent No. 7524942 (Mar. 13, 2025).

Notice of Reasons for Revocation issued in Japanese Patent Application No. 2022-518532/Patent No. 7524942, date of mailing: Jun. 19, 2025, 16 pages with partial translation.

International Search Report for PCT/JP2020/018241 (Jun. 16, 2020).

* cited by examiner

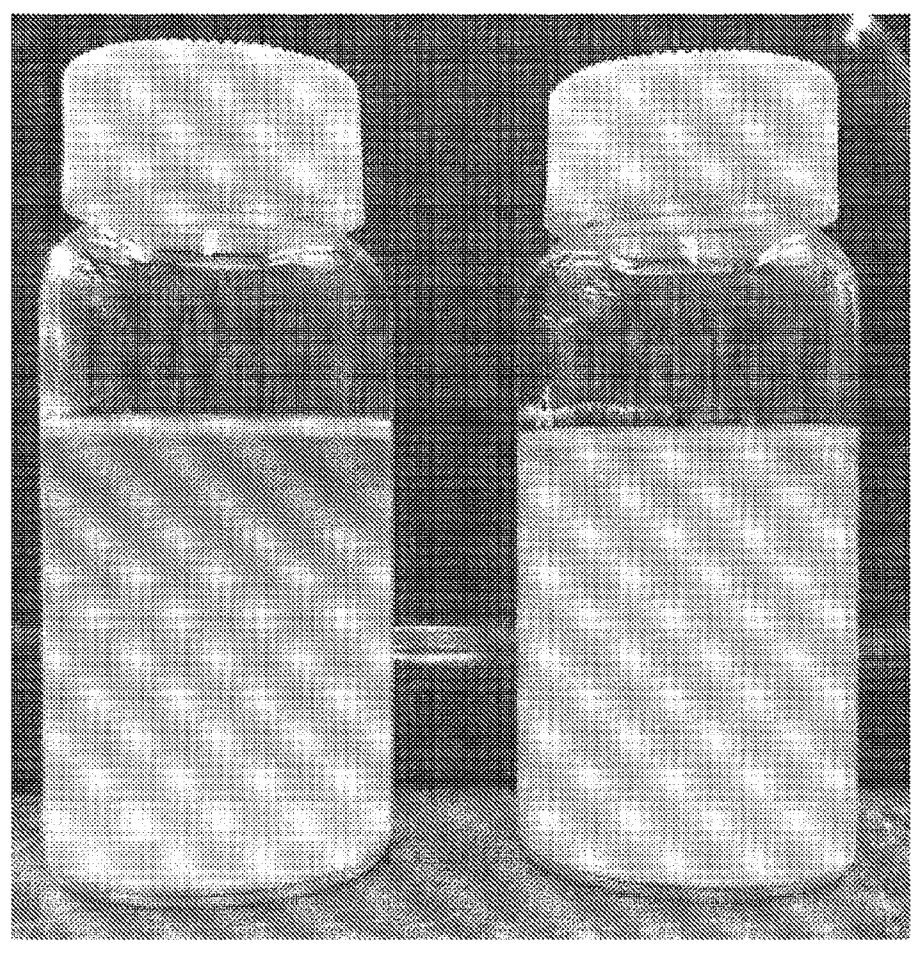

SURFACE-MODIFIED ZINC OXIDE PARTICLES, LIQUID DISPERSION, AND COSMETIC

This application is a National Stage Application of PCT/JP2020/018241, filed Apr. 30, 2020, the contents of which are incorporated herein by reference. To the extent appropriate, a claim of priority is made to the above disclosed application.

TECHNICAL FIELD

The present invention relates to surface-modified zinc oxide particles, a liquid dispersion, and a cosmetic.

BACKGROUND ART

It is known that zinc oxide has an excellent ultraviolet shielding capability, high gas barrier properties, and, furthermore, high transparency. Therefore, particles made of zinc oxide as a forming material (hereinafter, referred to as "zinc oxide particles") have functions of ultraviolet shielding, gas barrier, or the like and are used as a forming material of various materials that require transparency. Examples of such materials include ultraviolet shielding films, ultraviolet shielding glasses, cosmetics, gas barrier films, and the like.

As a method for the above-described various materials to obtain transparency, for example, a method for reducing the primary particle diameters of zinc oxide particles, which are a forming material, is exemplified. As the method for reducing the primary particle diameters of zinc oxide particles, various methods such as a thermal decomposition method and a vapor phase method are being studied (for example, refer to Patent Literature Nos. 1 and 2).

In a case where zinc oxide particles are applied to cosmetics, a surface treatment is performed on the zinc oxide particles in order to adapt the surfaces of the zinc oxide particles to the properties of cosmetic products or suppress the catalytic activity of the zinc oxide particles.

In a case where zinc oxide particles are blended with oily cosmetics, emulsion-type oil phases, or the like, zinc oxide particles having alkoxy groups on the surfaces by treating the surfaces with a silane coupling agent or the like having an alkoxy group are used (for example, refer to Patent Literature Nos. 3 and 4).

In the following description, zinc oxide particles having a silane coupling agent on the surfaces will be referred to as surface-modified zinc oxide particles.

Such surface-modified zinc oxide particles are blended with cosmetics as they are or blended with cosmetics in a state of a liquid dispersion in which the zinc oxide particles are dispersed in a dispersion medium.

CITATION LIST

Patent Literature

[Patent Literature No. 1] Japanese Laid-open Patent Publication No. 2002-294527

[Patent Literature No. 2] Japanese Laid-open Patent Publication No. 2000-95519

[Patent Literature No. 3] Pamphlet of International Publication No. WO 2017/130632

[Patent Literature No. 4] Japanese Laid-open Patent Publication No. 2007-51188

SUMMARY OF INVENTION

Technical Problem

However, a large amount of dispersion energy was required to blend even zinc oxide particles having a silane coupling agent on the surfaces with oily cosmetics. In addition, there is a problem in that, even when the zinc oxide particles are blended with oily cosmetics, transparency and ultraviolet shielding properties cannot be sufficiently obtained.

The present invention has been made in view of the above circumstances, and an object of the present invention is to provide surface-modified zinc oxide particles that are easily blended with oily cosmetics and are excellent in terms of transparency and ultraviolet shielding properties. In addition, another object of the present invention is to provide a liquid dispersion and a cosmetic that contain such surface-modified zinc oxide particles.

Solution to Problem

In order to solve the above problems, a first aspect of the present invention provides surface-modified zinc oxide particles, wherein the surface-modified zinc oxide particles have a silane coupling agent having an alkoxy group on surfaces thereof, and a particle diameter d50 thereof is 4 μm or less, wherein the particle diameter d50 is obtained when the zinc oxide particles is measured with a laser diffraction/scattering type particle size distribution-measuring instrument by a following measurement method and a cumulative volume percentage of a particle size distribution thereof is 50%.

(The Measurement Method)

10 g of the surface-modified zinc oxide particles, 88 g of cyclopentasiloxane, and 2 g of polyglyceryl-3 polydimethylsiloxyethyl dimethicone are mixed to obtain a liquid mixture, a dispersion treatment is performed on the obtained liquid mixture at 9,500 rpm for 5 minutes using a homogenizer to obtain a liquid dispersion, the liquid dispersion is diluted with cyclopentasiloxane so that a content of the surface-modified zinc oxide particles in the obtained liquid dispersion is 0.01% by mass to produce a measurement solution, and d50 is measured with the laser diffraction/scattering type particle size distribution-measuring instrument using the obtained measurement solution.

In the first aspect of the present invention, b* in an L*a*b* colorimetric system chromaticity diagram of the surface-modified zinc oxide particles may be 4.0 or more and 18 or less.

In the first aspect of the present invention, the silane coupling agent may be at least one selected from a group consisting of an alkylalkoxysilane, an allylalkoxysilane, a polysiloxane having an alkyl group in a side chain, and a polysiloxane having an allyl group in a side chain.

In the first aspect of the present invention, the silane coupling agent may be at least one selected from a group consisting of octyltriethoxysilane, octyltrimethoxysilane, and a dimethoxydiphenylsilane-triethoxycaprylylsilane crosspolymer.

In order to solve the above problems, a second aspect of the present invention provides a liquid dispersion containing the above surface-modified zinc oxide particles and a dispersion medium.

In order to solve the above problems, a third aspect of the present invention provides a cosmetic containing the above surface-modified zinc oxide particles and at least one selected from the group consisting of the above dispersions.

In order to solve the above problems, a fourth aspect of the present invention provides a method for selecting surface-modified zinc oxide particles which are the aforementioned surface-modified zinc oxide particles. The method of the fourth aspect is a method which comprises; preparing surface-modified zinc oxide particles having a silane coupling agent having an alkoxy group on surfaces thereof, mixing 10 g of the surface-modified zinc oxide particles, 88 g of cyclopentasiloxane, and 2 g of polyglyceryl-3 polydimethylsiloxyethyl dimethicone to obtain a liquid mixture, performing a dispersion treatment on the obtained liquid mixture at 9,500 rpm for 5 minutes using a homogenizer to obtain a liquid dispersion, producing a measurement solution by diluting the obtained liquid dispersion with cyclopentasiloxane so that a content of the surface-modified zinc oxide particles in the liquid dispersion is 0.01% by mass, measuring a particle diameter d50, which is obtained when a cumulative volume percentage of a particle size distribution thereof is 50%, with a laser diffraction/scattering type particle size distribution-measuring instrument using the obtained measurement solution, determining whether or not the d50 is 4 μm or less, and selecting the surface-modified zinc oxide particles in a case where the d50 is 4 μm or less.

In order to solve the above problems, a fifth aspect of the present invention provides a method for producing surface-modified zinc oxide particles which are the aforementioned surface-modified zinc oxide particles.

The method of the fifth aspect is a method which comprises; a step of putting a silane coupling agent having an alkoxy group, a solvent, and zinc oxide particles into a disperser to produce a liquid mixture and a step of dispersing the liquid mixture with the disperser to obtain surface-modified zinc oxide particles of which d50 thereof is 4 μm or less, in which, in the step wherein the liquid mixture is produced, a solvent content in the liquid mixture is 40% by mass or more and 95% by mass or less.

Advantageous Effects of Invention

According to the present invention, it is possible to provide surface-modified zinc oxide particles that can be dispersed in cosmetics with a small amount of energy and are excellent in terms of transparency and ultraviolet shielding properties. In addition, according to the present invention, it is possible to provide a liquid dispersion and a cosmetic which contain such surface-modified zinc oxide particles.

BRIEF DESCRIPTION OF DRAWINGS

FIG. 1 is a view showing the dispersion states of surface-modified zinc oxide particles of Example 4 (right) and Comparative Example 2 (left).

DESCRIPTION OF EMBODIMENTS

An embodiment of a method for producing surface-modified zinc oxide particles of the present invention will be described.

The present embodiment is simply a specific description for better understanding of the gist of the invention and does not limit the present invention unless particularly otherwise described. Numerical values, amounts, materials, types, times, temperatures, orders, and the like can be changed, omitted, replaced, added, and the like in the present invention within the scope of the gist.

[Surface-Modified Zinc Oxide Particles]

Surface-modified zinc oxide particles of the present embodiment are surface-modified zinc oxide particles having a silane coupling agent having an alkoxy group on the surfaces. In addition, in the particles, the particle diameter d50 when the cumulative volume percentage of the particle size distribution is 50% when measured with a laser diffraction/scattering type particle size distribution-measuring instrument by the following measurement method is 4 μm or less.

(The Measurement Method)

10 g of the surface-modified zinc oxide particles, 88 g of cyclopentasiloxane, and 2 g of polyglyceryl-3 polydimethylsiloxyethyl dimethicone are mixed to obtain a liquid mixture, a dispersion treatment is performed on the obtained liquid mixture at 9,500 rpm for 5 minutes using a homogenizer to obtain a liquid dispersion, the liquid dispersion is diluted with cyclopentasiloxane such that a content of the surface-modified zinc oxide particles in the obtained liquid dispersion is 0.01% by mass to produce a measurement solution, and d50 is measured with the laser diffraction/scattering type particle size distribution-measuring instrument using the obtained measurement solution.

Here, as cyclopentasiloxane, model number DOWSIL S 245 Fluid manufactured by Dow Toray Co., Ltd. may be used, and, as polyglyceryl-3 polydimethylsiloxyethyl dimethicone, KF-6106 manufactured by Shin-Etsu Chemical Co., Ltd. may be used.

Cyclopentasiloxane is a solvent that is commonly used in oily cosmetics. Therefore, it can be judged that surface-modified zinc oxide particles that are easily dispersed in cyclopentasiloxane are easily dispersed in oily cosmetics. Therefore, cyclopentasiloxane was used as a solvent for evaluation.

Polyglyceryl-3 polydimethylsiloxyethyl dimethicone is a dispersant that is commonly used in oily cosmetics. Therefore, when surface-modified zinc oxide particles are easily dispersed in cyclopentasiloxane using 2 g (2% by mass) of this dispersant, it can be judged that the surface-modified zinc oxide particles are easily dispersed in oily cosmetics.

Here, "being easily dispersed" means that a liquid dispersion having small dispersed particle diameters can be obtained with weak dispersion energy. Surface-modified zinc oxide particles having small dispersed particle diameters are excellent in terms of transparency and ultraviolet shielding properties when blended with cosmetics.

The reason for mixing 10 g (10% by mass) of the surface-modified zinc oxide particles in the evaluation is that, when the content of the surface-modified zinc oxide particles in the liquid dispersion is 10% by mass, the amount is a sufficiently appropriate amount for evaluating the dispersibility. That is, when the content of the surface-modified zinc oxide particles in the liquid dispersion is less than 10% by mass, the amount of the surface-modified zinc oxide particles to be dispersed is too small, and there are cases where differences are difficult to tell. On the other hand, even when the content of the surface-modified zinc oxide particles is set to an amount exceeding 10% by mass, the content is too large to enable appropriate evaluation or the tendency of dispersibility does not change, and thus there is no benefit of setting the content to an amount exceeding 10% by mass.

The condition of 9,500 rpm for the homogenizer is weak as a force to disperse powders. Therefore, if the dispersed particle diameters are small when the surface-modified zinc oxide particles have been dispersed with this degree of force, the surface-modified zinc oxide particles can be evaluated to be excellent in terms of dispersibility.

The reason for setting the dispersion treatment time to 5 minutes is that surface-modified zinc oxide particles having large dispersed particle diameters when dispersed for 5 minutes using a homogenizer under a condition of 9,500 rpm can be evaluated to be not excellent in terms of dispersibility. As the homogenizer, a common stirring type homogenizer that can be used to disperse particles can be used. As a specific example, for example, a homogenizer such as ULTRA-TURRAX (registered trademark) series T25 basic (manufactured by IVA) can be preferably used.

Surface-modified zinc oxide particles of the present embodiment are surface-modified zinc oxide particles having a silane coupling agent having an alkoxy group on the surfaces. That is, the surface-modified zinc oxide particles of the present embodiment are zinc oxide particles having a silane coupling agent having an alkoxy group attached to at least part of the surfaces.

The specific surface area of the zinc oxide particles of the present embodiment can be arbitrarily selected, but is preferably 1.5 $m^2/g$ or more, more preferably 2.5 $m^2/g$ or more, and still more preferable 4 $m^2/g$ or more. In addition, the specific surface area of the surface-modified zinc oxide particles may be, for example, 55 $m^2/g$ or less and is preferably 50 $m^2/g$ or less and more preferably 45 $m^2/g$ or less. The specific surface area of the surface-modified zinc oxide particles may be 40 $m^2/g$ or less, may be 30 $m^2/g$ or less, or 30 $m^2/g$ or less as necessary. The upper limit value and lower limit value of the specific surface area of the zinc oxide particles can be arbitrarily combined together.

When the specific surface area of the zinc oxide particles is 1.5 $m^2/g$ or more and 50 $m^2/g$ or less, the surface-modified zinc oxide particles are excellent in terms of transparency and ultraviolet shielding properties in the case of being blended with cosmetics.

In a case where there is a desire to enhance the transparency in the case of blending the zinc oxide particles with cosmetics, the specific surface area of the surface-modified zinc oxide particles is preferably 8 $m^2/g$ or more, more preferably 15 $m^2/g$ or more, and still more preferable 20 $m^2/g$ or more.

For example, the specific surface area of the surface-modified zinc oxide particles is 20 $m^2/g$ or more and 50 $m^2/g$ or less, preferably 20 $m^2/g$ or more and 48 $m^2/g$ or less, and more preferably 20 $m^2/g$ or more and 46 $m^2/g$ or less. The specific surface area may be 20.0 $m^2/g$ or more and 30.0 $m^2/g$ or less, 20.0 $m^2/g$ or more and 38.0 nm/g or less, or 20.0 We/g or more and 44.0 $m^2/g$ or less.

In a case where the specific surface area of the surface-modified zinc oxide particles is 20 $m^2/g$ or more, when the surface-modified zinc oxide particles are blended with oily cosmetics containing silicone oil or the like, it is possible to obtain cosmetics having excellent transparency. On the other hand, when the specific surface area of the surface-modified zinc oxide particles is 50 $m^2/g$ or less, since the surface energy of the particles is not too large, it is possible to blend the surface-modified zinc oxide particles with oily cosmetics (hereinafter, abbreviated as "cosmetics" in some cases) with a small amount of energy.

On the other hand, in a case where there is a desire to enhance the ultraviolet shielding properties in the UVA region in the case of blending the zinc oxide particles with cosmetics, the specific surface area of the surface-modified zinc oxide particles is preferably less than 20 $m^2/g$, more preferably 15 $m^2/g$ or less, and still more preferably 8 $m^2/g$ or less.

For example, the specific surface area of the surface-modified zinc oxide particles is preferably 1.5 $m^2/g$ or more and less than 20 $m^2/g$, more preferably 1.5 $m^2/g$ or more and 15 $m^2/g$ or less, and still more preferably 1.5 $m^2/g$ or more and 8 $m^2/g$ or less.

In a case where the specific surface area of the surface-modified zinc oxide particles is 1.5 $m^2/g$ or more, when the surface-modified zinc oxide particles are blended with oily cosmetics containing silicone oil or the like, it is possible to obtain transparent cosmetics. On the other hand, when the specific surface area of the surface-modified zinc oxide particles is less than 20 $m^2/g$, since the surface energy of the particles is not too large, it is possible to blend the surface-modified zinc oxide particles with a small amount of energy and to obtain cosmetics having excellent ultraviolet shielding properties in the UVA region.

The specific surface area (unit: $m^2/g$) of the surface-modified zinc oxide particles in the present embodiment is the BET specific surface area obtained by the BET method.

Examples of a method for measuring the specific surface area of the surface-modified zinc oxide particles include a BET method in which a full automatic specific surface area-measuring instrument (trade name: Macsorb HM Model-1201, manufactured by Mountech Co., Ltd.) is used.

In the surface-modified zinc oxide particles of the present embodiment, the particle diameter (d50) (hereinafter, abbreviated as "d50" in some cases) when the cumulative volume percentage of the particle size distribution is 50% in the above measurement method is preferably 4.00 μm or less, more preferably 1.00 μm or less, still more preferably 0.60 μm or less, and particularly preferably 0.40 μm or less. These values may be 2.00 μm or less, 0.50 μm or less, 0.30 μm or less, 0.20 μm or less, 0.10 μm or less, or 0.08 μm or less as necessary.

d50 is preferably as small as possible but cannot be equal to or less than the primary particle diameters of the surface-modified zinc oxide particles. Therefore, the lower limit value of d50 may be 0.02 μm, may be 0.05 μm, or may be 0.10 μm. The lower limit may be 0.03 μm, 0.06 μm, or 0.08 μm as necessary.

The primary particle diameters may be, for example, the average value of the maximum diameters (maximum major axes) of the respective surface-modified zinc oxide particles, for example, 100 particles obtained by observation using a transmission electron microscope or the like. The primary particle diameters of the surface-modified zinc oxide particles can be arbitrarily selected and may be, for example, 21 ram to 713 nm. In a case where there is a desire to enhance the transparency in the case of blending the surface-modified zinc oxide particles with cosmetics, the primary particle diameters are preferably 22 nm to 54 nm and more preferably 23 nm to 54 nm. In a case where there is a desire to enhance the ultraviolet shielding properties in the UVA region in the case of blending the surface-modified zinc oxide particles with cosmetics, the primary particle diameters are, for example, preferably 54 nm to 713 nm, more preferably 71 nm to 713 nm, and still more preferably 134 nm to 713 nm. However, the primary particle diameters are not limited only to these examples.

In the measurement method of the present embodiment, as the laser diffraction/scattering type particle size distribution-measuring instrument, model number LA-920 manufactured by Horiba, Ltd. was used, but the measuring instrument is not limited thereto, and a well-known instrument may be used.

Hereinafter, the reason for the surface-modified zinc oxide particles where d50 becomes 4 μm or less in the evaluation by the above measurement method to be dispersible in oily cosmetics with a small amount of energy and to have excellent ultraviolet shielding properties will be described.

The present inventors and the like found that excellent surface-modified zinc oxide particles that can be easily dispersed in cosmetics containing silicone can be obtained as a result of performing a dispersion treatment with high energy on zinc oxide particles and a silane coupling agent having an alkoxy group (hereinafter, abbreviated as "silane coupling agent" in some cases) using a disperser having large dispersion energy ouch as a bead mill at the time of a surface treatment of the zinc oxide particles with the silane coupling agent. Here, the dispersion energy refers to energy required to disperse the zinc oxide particles in a solvent using the silane coupling agent. In other words, the dispersion energy is energy large enough to loosen agglomerated zinc oxide particles.

The detailed mechanism is assumed as described below.

The zinc oxide particles having a specific surface area of 1.5 $m^2/g$ or more and 50 $m^2/g$ or less are likely to agglomerate with one another. In particular, the zinc oxide particles having a specific surface area of 20 $m^2/g$ or more and 50 $m^2/g$ or less are more likely to agglomerate with one another. Therefore, conventionally, the surfaces were treated with a silane coupling agent in an agglomerated state. However, when particles surface-treated in a state where the particles have agglomerated with one another as conventional particles and an oil component of an oily cosmetic are mixed with each other, the particles are dispersed in the agglomerated state. Therefore, the transparency and the ultraviolet shielding properties deteriorate due to the agglomeration. In order to prevent the above-described deterioration, there is a need to loosen the agglomeration of the particles, and a larger amount of dispersion energy was required at the time of producing oily cosmetics. However, even when the transparency and the ultraviolet shielding properties were improved by loosening the agglomeration with high energy, since the agglomeration of agglomerates surface-treated in an agglomerated state had been loosened, the surface treatment state of the surfaces of the loosened zinc oxide particles became uneven. As a result, the dispersion stability of the surface-modified zinc oxide particles in oily cosmetics was impaired.

However, it is assumed that, when zinc oxide particles are dispersed in a solvent with high energy, it is possible to treat the surfaces with a silane coupling agent in a state where the agglomeration of the zinc oxide particles has been loosened and the silane coupling agent can be present substantially uniformly on the entire surfaces of the zinc oxide particles. Therefore, when surface-modified zinc oxide particles in such a state and an oil component are mixed with each other, any part of the surfaces of the zinc oxide particles is familiar to the oil component, and the particles can be dispersed in the oil component with low energy. In addition, since the silane coupling agent is present substantially uniformly on the surfaces of the zinc oxide particles, it is assumed that agglomeration of the surface-modified zinc oxide particles is suppressed and it is possible to obtain cosmetics being excellent in terms of transparency, ultraviolet shielding properties, and dispersion stability.

However, it is extremely difficult to directly confirm that the silane coupling agent is uniformly present on the surfaces of the zinc oxide particles. In the present embodiment, an effect of enabling the easy dispersion of the surface-modified zinc oxide particles in solvents is assumed to develop due to a complex combination of a number of factors, specifically, a complex combination of a number of factors such as the shapes, specific surface area, and particle size distribution of the zinc oxide particles, the degree of hydrolysis of the silane coupling agent having an alkoxy group, the condition of attachment of the silane coupling agent having an alkoxy group to the zinc oxide particles, and the attachment rate of the silane coupling agent having an alkoxy group to the zinc oxide particles. Therefore, it is considered that it is almost impossible to directly specify the characteristics of the surface-modified zinc oxide particles of the present embodiment with the state of the surfaces of the zinc oxide particles surface-modified with the silane coupling agent having an alkoxy group.

Therefore, as a result of various studies, the present inventors and the like found that, when the surfaces of the zinc oxide particles are treated with the silane coupling agent with high energy until d50 becomes 4 μm or less by the above-described measurement method, that is, such that intended dispersibility is achieved, surface-modified zinc oxide particles that are easily dispersed in oily cosmetics and have excellent ultraviolet shielding properties can be obtained. In other words, the value of d50 that is obtained by the above measurement method may be considered as an index of whether or not the silane coupling agent is uniformly present on the surfaces of the zinc oxide particles.

In the present embodiment, since the surface-modified zinc oxide particles that are preferably used in cosmetics are used, an index for evaluating the state of the surface treatment was obtained using zinc oxide particles as the particles, a silane coupling agent having an alkoxy group as a surface modification material, cyclopentasiloxane as a dispersion medium, and polyglyceryl-3 polydimethylsiloxyethyl dimethicone as a dispersant.

However, a method for evaluating the surface treatment state of the present embodiment is not limited to the combination of zinc oxide particles and a silane coupling agent having an alkoxy group and can be applied to an extended range of particles and a surface modification material. That is, a dispersion medium that is desired to be used for dispersion is selected, and a dispersant is used for dispersion as necessary. In addition, an index of the uniformity of the surface treatment can be obtained by dispersing particles surface-modified with a surface modification agent in the dispersion medium with weak dispersion energy and measuring the magnitude of the dispersed particle diameters in a liquid dispersion.

When the surface treatment with a silane coupling agent is performed with high energy, as a result of the progress of the surface treatment, b* in the L*a*b* colorimetric system chromaticity diagram of the surface-modified zinc oxide particles (hereinafter, abbreviated as "b*" in some cases) becomes larger than b* of the zinc oxide particles before the surface treatment. Therefore, b* of the surface-modified zinc oxide particles becomes an index of the surface treatment with the silane coupling agent.

In the surface-modified zinc oxide particles of the present embodiment, b* is preferably 4.0 or more and 18 or less and more preferably 4.5 or more and 16 or less. b* may be 4.0 or more and 12 or less, 4.5 or more and 11 or less, or 5.0 or more and 10.0 or less as necessary. The difference in b* of the particles between before surface modification and after surface modification may be, for example, 0.5 to 8.0, may be 1.0 to 8.0, may be 2.0 to 8.0, or may be 3.0 to 7.5. However, the difference is not limited only to these values.

As a method for measuring b* of the surface-modified zinc oxide particles, a well-known method such as the use of a spectral colorimeter, for example, a spectral colorimeter (manufactured by Nippon Denshoku Industries Co., Ltd., Spectro Color Meter SE7700) can be used.

In the present embodiment, "having the silane coupling agent on the surfaces" means that the silane coupling agent is in contact with or bonds to the zinc oxide particles due to an interaction therebetween. As the contact, for example, physical adsorption is exemplified. In addition, as the bond, an ionic bond, a hydrogen bond, a covalent bond, and the like are exemplified.

The amount of the silane coupling agent in the surface-modified zinc oxide particles may be appropriately adjusted in accordance with the specific surface area of the zinc oxide particles and the degree of hydrophobilization of an oily cosmetic to be blended before use. For example, the amount of the silane coupling agent in the surface-modified zinc oxide particles is preferably 1% by mass or more and 20% by mass or less, more preferably 2% by mass or more and 16% by mass or less, and still more preferably 3% by mass or more and 16% by mass or less relative to the zinc oxide particles. The amount may be 3% by mass or more and 8% by mass or less, 5% by mass or more and 10% by mass or less or the like as necessary. However, the amount is not limited only to the examples.

The amount of the silane coupling agent in the surface-modified zinc oxide particles can be calculated by, for example, quantitatively analyzing the amount of Si in the surface-modified zinc oxide particles with an inductively coupled plasma atomic emission spectrometer.

"Zinc Oxide Particles"

The zinc oxide particles (before the surface treatment) of the present embodiment can be arbitrarily selected, but preferably have 1.5 $m^2/g$ or more, more preferably 2.5 $m^2/g$ or more, and still more preferable 4 $m^2/g$ or more. In addition, the specific surface area of the zinc oxide particles is preferably 50 $m^2/g$ or less and more preferably 45 $m^2/g$ or less. The specific surface area of the zinc oxide particles may be 40 $m^2/g$ or less, may be 30 m/g or less, or 10 $m^2/g$ or less as necessary.

The specific surface area of the zinc oxide particles before the surface treatment and the specific surface area of the surface-modified zinc oxide particles slightly vary depending on how the silane coupling agent is attached, but do not change significantly.

Therefore, in order to obtain surface-modified zinc oxide particles having a desired specific surface area, zinc oxide particles having a desired specific surface area needs to be used. That is, it is possible for the surface-modified zinc oxide particles of the present embodiment to preferably have the same value or range as the above-described preferable value or range of the specific surface area of the zinc oxide particles.

b* in the L*a*b* colorimetric system chromaticity diagram of the zinc oxide particles before the treatment is preferably 10 or less. When zinc oxide particles having b* in the above range are used, b* of the surface-modified zinc oxide particles can also be in the above range, that is, 4.0 or more and 18 or less, and b* of the surface-modified zinc oxide particles becomes larger than b* of the zinc oxide particles before the surface treatment. As a result, it is possible to suppress the surface-modified zinc oxide particles to yellowness at which the surface-modified zinc oxide particles can be applied to cosmetics. The lower limit value of b of the zinc oxide particles is not particularly limited and may be 0, may be 1.0, or may be 1.5.

"Silane Coupling Agent Having Alkoxy Group"

The silane coupling agent having an alkoxy group can be arbitrarily selected, and preferable examples thereof include silane coupling agents represented by the following general formula (1) that can be used in cosmetics.

$$R^1Si(OR^2)_2 \quad (1)$$

($R^1$ represents an alkyl group, fluoroalkyl group or phenyl group having 1 to 18 carbon atoms, and $R^2$ represents an alkyl group having 1 to 4 carbon atoms.)

Such a silane coupling agent is preferably at least one selected from the group consisting of an alkylalkoxysilane, an allylalkoxysilane, a polysiloxane having an alkyl group in a side chain, and a polysiloxane having an allyl group in a side chain.

Examples of the alkylalkoxysilane include methyltrimethoxysilane, methyltriethoxysilane, methyltripropoxysilane, methyltributoxysilane, ethyltrimethoxysilane, ethyltriethoxysilane, ethyltripropoxysilane, ethyltributoxysilane, n-propyltrimethoxysilane, n-propyltriethoxysilane, n-propyltripropoxysilane, n-propyltributoxysilane, isopropyltrimethoxysilane, isopropyltriethoxysilane, isopropyltripropoxysilane, isopropyltributoxysilane, phenyltrimethoxysilane, phenyltriethoxysilane, phenyltripropoxysilane, phenyltributoxysilane, n-octyltrimethoxysilane, n-octyltriethoxysilane (triethoxycaprylylsilane), n-octadecyltrimethoxysilane, and the like.

As the silane coupling agent, it is also possible to use, for example, polymer-type silane coupling agents and the like having a siloxane skeleton as the main chain and having an alkoxy group and an acrylic group in the molecular structure such as dimethoxydiphenylsilane-triethoxycaprylylsilane crosspolymers, triethoxysilylethyl polydimethylsiloxyethyl dimethicone, and triethoxysilylethyl polydimethylsiloxyethyl hexyl dimethicone.

As the silane coupling agent, it is also possible to use fluoroalkylalkoxysilanes and the like such as trifluoropropyltrimethoxysilane, perfluorooctyltriethoxysilane, and tridecafluorooctyltriethoxysilane.

These silane coupling agents may be used singly or two or more silane coupling agents may be mixed and used.

Among the above-described silane coupling agents, silane coupling agents having an octyl group in the molecule are more preferable. Specifically, silane coupling agents that are compatible with oil phases with a wide range of polarity, from natural oils or ester oils to silicone oils, are more preferable. As such silane coupling agents, at least one selected from the group consisting of n-octyltriethoxysilane, n-octyltrimethoxysilane, and a dimethoxydiphenylsilane-triethoxycaprylylsilane crosspolymer is particularly preferable.

These silane coupling agents may be used singly or two or more silane coupling agents may be mixed and used.

In the surface-modified zinc oxide particles of the present embodiment, the zinc oxide particles may be surface-treated using, in addition to the silane coupling agent, a surface treatment agent that is used for cosmetics and is not a silane coupling agent as long as the characteristics of the surface-modified zinc oxide particles are not impaired.

Examples of the surface treatment agent that is not a silane coupling agent include an inorganic material such as silica or alumina and an organic material such as a silicone compound, a fatty acid, a fatty acid soap, a fatty acid ester, or an organic titanate compound.

"Method for Producing Surface-Modified Zinc Oxide Particles"

A method for producing surface-modified zinc oxide particles of the present embodiment has a step of putting a silane coupling agent having an alkoxy group, a solvent, and zinc oxide particles into a disperser to produce a liquid mixture and a step of dispersing this liquid mixture with a predetermined amount of energy or more.

The step of producing the liquid mixture may further include water.

The step of producing the liquid mixture may further include a catalyst.

A heating step may be performed after the dispersion treatment step.

A drying step may be performed after the dispersion treatment step or after the heating step.

After the heating step or after the drying step, a cracking treatment may be performed.

As the silane coupling agent having an alkoxy group and the zinc oxide particles that are used in the production method, the same silane coupling agent and zinc oxide particles as described above can be used. Therefore, the silane coupling agent and the zinc oxide particles will not be described again.

"Production Step of Liquid Mixture"

In the production step of a liquid mixture, a silane coupling agent, a solvent, and zinc oxide particles are put into a disperser. Furthermore, pure water or a catalyst may be put in as necessary. These materials may be put in simultaneously or sequentially. The order of putting in these materials is not particularly limited. After being put into the disperser, the materials may not be stirred or may be simply stirred. In addition, before being put into a liquid dispersion, these materials may be mixed in advance and then put into the disperser.

"Solvent"

The solvent is not particularly limited as long as the solvent is miscible with the silane coupling agent. Examples of the solvent include alcohols such as methanol, ethanol, n-propanol, isopropanol, and n-butanol, esters such as ethyl acetate and butyl acetate, n-hexane, toluene, xylene, and the like. Among these solvents, alcohols are preferable since alcohols are miscible with water, and, among alcohols, isopropanol is particularly preferable.

The content of the solvent in the liquid mixture can be arbitrarily selected, but is preferably 40% by mass or more in order to suppress agglomeration of the zinc oxide particles. The upper limit value of the content of the solvent is not particularly limited, but is preferably 95% by mass or less from the viewpoint of the production efficiency.

The content of the zinc oxide particles in the liquid mixture can be arbitrarily selected, but is preferably 1% by mass or more and 55% by mass or less and more preferably 10% by mass or more and 50% by mass or less from the viewpoint of satisfying both the suppression of agglomeration of the zinc oxide particles and the production efficiency. The content may be 15% by mass or more and 45% by mass or less, 20% by mass or more and 40% by mass or less, or 25% by mass or more and 35% by mass or less.

The content of the silane coupling agent in the liquid mixture can be arbitrarily selected and may be appropriately adjusted so that desired hydrophobicity can be imparted to the zinc oxide particles. For example, the silane coupling agent may be adjusted and mixed such that the amount of the silane coupling agent in the surface-modified zinc oxide particles becomes 1% by mass or more and 20% by mass or less. The amount may be 1% by mass or more and 10% by mass or less or 1% by mass or more and 5% by mass or less as necessary. The content of the silane coupling agent in the liquid mixture may be, for example, 0.01% by mass or more and 11% by mass or less or 0.1% by mass or more and 10% by mass or less.

The amount of pure water can be arbitrarily selected, and it is preferable to appropriately adjust and put in an amount of pure water necessary to promote the hydrolysis reaction of the silane coupling agent.

The amount of the catalyst can be arbitrarily selected, and it is preferable to appropriately adjust and put in an amount of the catalyst necessary to promote the hydrolysis reaction of the silane coupling agent. The catalyst may be an acid or may be a base.

Examples of the acid include inorganic acids such as hydrochloric acid, hydrobromic acid, hydroiodic acid, sulfuric acid, nitric acid, boric acid, and phosphoric acid and organic acids such as acetic acid, citric acid and formic acid. These acids may be used singly or two or more acids may be used in combination.

Examples of the base include sodium hydroxide, potassium hydroxide, barium hydroxide, calcium hydroxide, ammonia, amines, and the like. These bases may be used singly or two or more bases may be used in combination.

"Disperser"

The disperser is not particularly limited as long as the disperser is capable of imparting dispersion energy to the liquid mixture to an extent that the surface treatment can be performed while loosening the agglomeration of the zinc oxide particles.

Examples of such a disperser include a colloid mill, a roll mill, an ultrasonic disperser, a high-pressure homogenizer, an ultimizer, a rotary mill, a planetary mill, a bead mill, a sand mill, and the like. As dispersion media that are used in dispersion apparatuses in which dispersion media are used, it is possible to use, for example, granules having predetermined hardness of zirconia, glass, alumina, titania, silicon nitride, or the like.

"Dispersion Step"

In the dispersion step, the liquid mixture is dispersed using the disperser with a predetermined amount of energy or more to obtain surface-modified zinc oxide particles.

The energy that is imparted to the liquid mixture may be appropriately adjusted according to the size of the disperser. Therefore, conditions for the dispersion may be selected as appropriate. For example, in a case where the dispersion treatment is performed with a mill, for example, a bead mill using a container having a capacity of about 1 L, it is preferable to perform the dispersion treatment at a rotation speed of 500 rpm or faster for 1 hour or longer and 10 hours or shorter. Here, the conditions can be selected as necessary and are not limited only to the above conditions.

In addition, in a case where the dispersion treatment is performed with a mill, for example, a bead mill using a container having a capacity of about 1 L, the dispersion energy that is imparted to the liquid mixture is, for example, preferably 100 W·h/kg or more and 600 W·h/kg or less. Here, the conditions can be selected as necessary and are not limited only to the above conditions.

In addition, since the cracking force of the bead mill depends on the centrifugal force of a disc or beads on the pin outer periphery in the mill, when the product (impulse) of the centrifugal force and the dispersion time is calculated in a case where the total weight of the beads in the mill is regarded as the bead weight, the dispersion treatment is preferably performed such that the product becomes $0.5 \times 10^6$ N·s or more and $100 \times 10^6$ N·s or less.

In addition, the dispersion treatment may be performed until b of the surface-modified zinc oxide particles becomes 4.0 or more and 18 or less. In this case, the degree of progress of the dispersion treatment may be confirmed by extracting a small amount of the zinc oxide particles during the dispersion treatment and measuring b* of the zinc oxide particles using a spectral colorimeter.

The temperature in the dispersion step is not particularly limited, but is, for example, preferably 20° C. or higher and 45° C. or lower.

In the present invention, the surface-modified zinc oxide particles of the present invention may be obtained by, in a method having a step of putting a silane coupling agent having an alkoxy group, a solvent (dispersion medium), and zinc oxide particles into a disperser to produce a liquid mixture and a step of dispersing the liquid mixture with the disperser to obtain surface-modified zinc oxide particles of which d50 is 4 μm or less, adjusting the solvent content in the liquid mixture so as to be 40% by mass or more and 95% by mass or less in the step of producing the liquid mixture. Here, d50 means a particle diameter measured by the following measurement method.

(The Measurement Method)

10 g of the surface-modified zinc oxide particles, E$ g of cyclopentasiloxane, and 2 g of polyglyceryl-3 polydimethylsiloxyethyl dimethicone are mixed to obtain a liquid mixture, a dispersion treatment is performed on the obtained liquid mixture at 9,500 rpm for 5 minutes using a homogenizer to obtain a liquid dispersion, the liquid dispersion is diluted with cyclopentasiloxane such that a content of the surface-modified zinc oxide particles in the obtained liquid dispersion is 0.01% by mass to produce a measurement solution, and d50 is measured with the laser diffraction/scattering type particle size distribution-measuring instrument using the obtained measurement solution.

Here, as cyclopentasiloxane, model number DOWSIL SH 245 Fluid manufactured by Dow Toray Co., Ltd. may be used, and, as polyglyceryl-3 polydimethylsiloxyethyl dimethicone, KF-6106 manufactured by Shin-Etsu Chemical Co., Ltd. may be used.

The dispersion energy required to obtain desired surface-modified zinc oxide particles varies depending on various conditions such as the kind of a dispersion apparatus to be used and the amount of the zinc oxide particles charged, and thus it is difficult to unambiguously determine the dispersion energy.

Therefore, it is also possible to confirm whether or not the dispersion energy is sufficient by measuring d50 of the obtained surface-modified zinc oxide particles by the above measurement method.

In addition, in the present invention, it is also possible to select preferable surface-modified zinc oxide particles by the following method. First, surface-modified zinc oxide particles having a silane coupling agent having an alkoxy group on the surfaces are prepared, and 10 g of the surface-modified zinc oxide particles, 88 g of cyclopentasiloxane, and 2 g of polyglyceryl-3 polydimethylsiloxyethyl dimethicone are mixed to obtain a liquid mixture. The obtained liquid mixture is dispersed using a homogenizer at 9,500 rpm for 5 minutes to obtain a liquid dispersion, and the obtained liquid dispersion is diluted with cyclopentasiloxane such that the content of the surface-modified zinc oxide particles in the liquid dispersion is 0.01% by mass to produce a measurement solution. The particle diameter d50 when the cumulative volume percentage of the particle size distribution is 50% is measured with a laser diffraction/scattering type particle size distribution-measuring instrument using the obtained measurement solution, and whether or not d50 is 4 μm or less is determined. In a case where d50 is 4 μm or less, the surface-modified zinc oxide particles can be selected as preferable particles.

"Heating Step"

From the viewpoint of promoting the surface treatment step of the silane coupling agent, a heating step may be performed at the same time as the dispersion step or after the dispersion step.

The heating temperature is not particularly limited as long as the surface treatment is promoted at the heating temperature and is, for example, preferably 40° C. or higher and 150° C. or lower. The heating temperature may be 40° C. or higher and 80° C. or lower, 60° C. to 100° C., or the like as necessary.

"Drying Step"

The liquid after the dispersion treatment is preferably dried using a drying apparatus. A treatment that shortens the drying time, such as solid-liquid separation, may be performed before drying. The drying apparatus is not particularly limited, and examples thereof include a box-like dryer, a vacuum dryer, a vibration dryer, a fluidized bed dryer, a band dryer, an evaporator, a NAUTA mixer, a Henschel mixer, a RIBOCONE, a paddle dryer, a spray dryer, a slurry dryer, a flash dryer, a rotary dryer, and the like.

The drying temperature is not particularly limited as long as the solvent can be removed, but is preferably, for example, 50° C. or higher and 200° C. or lower. The drying temperature may be 60° C. or higher and 150° C. or lower, 70° C. or higher and 120° C. or lower, or the like.

"Cracking Step"

The dried surface-modified zinc oxide particles may be cracked using a cracking device. The cracking device can be arbitrarily selected, and examples thereof include an atomizer, a hammer mill, a jet mill, an impeller mill, a pin mill, and the like. The cracking step makes it possible to suppress the rough feel of the surface-modified zinc oxide particles when, for example, the surface-modified zinc oxide particles are blended with cosmetics. That is, the cracking step makes it possible to improve usability when the surface-modified zinc oxide particles are used in cosmetics.

[Liquid Dispersion]

A liquid dispersion of the present embodiment contains the surface-modified zinc oxide particles of the present embodiment and a dispersion medium. The liquid dispersion may be formed by preparing the surface-modified zinc oxide particles of the present embodiment and mixing the surface-modified zinc oxide particles with a dispersion medium.

The liquid dispersion of the present embodiment also may preferably contain a paste-form dispersing element having a high viscosity.

The dispersion medium is not particularly limited as long as the surface-modified zinc oxide particles can be dispersed. In a case where the surface-modified zinc oxide particles are used for cosmetics, the dispersion medium is not particularly limited as long as the dispersion medium can be prescribed for cosmetics.

Examples of the dispersion medium include hydrophobic dispersion media such as chain-like polysiloxanes such as dimethylpolysiloxane, methylphenylpolysiloxane, and diphenylpolysiloxane; cyclic polysiloxanes such as octamethylcyclotetrasiloxane, decamethylcyclopentasiloxane, and dodecamethylcyclohexasiloxane; modified polysiloxane such as amino-modified polysiloxane, polyether-modified polysiloxane, alkyl-modified polysiloxane, and fluorine-modified polysiloxane, hydrocarbon oils such as liquid paraffin, squalane, isoparaffin, branched chain-like light paraffin, vaseline, ceresin, dodecane, isododecane, tridecane, tetradecane, hexadecane, isohexadecane, and octadecane; ester oils such as isopropyl myristate, cetyl isooctanoate, glyceryl trioctanoate, tri(caprylic acid/capric acid) glyceryl, and alkyl benzoate (C12-15); higher fatty acids such as lauric acid, myristic acid, palmitic acid, and stearic acid; higher alcohols such as lauryl alcohol, cetyl alcohol, stearyl alcohol, octyldodecanol, and isostearyl alcohol; and the like. In addition, examples thereof include alcohols such as methanol, ethanol, n-propanol, isopropanol, n-butanol, 2-butanol, octanol, and glycerin; ethers such as ethyl acetate, butyl acetate, ethyl lactate, propylene glycol monomethyl ether acetate, propylene glycol monoethyl ether acetate, and γ-butyrolactone; ethers such as diethyl ether, ethylene glycol, monomethyl ether (methyl cellosolve), ethylene glycol monoethyl ether (ethyl cellosolve), ethylene glycol monobutyl ether (butyl cellosolve), diethylene glycol monomethyl ether, and diethylene glycol monoethyl ether; aromatic hydrocarbons such as benzene, toluene, ethylbenzene, 1-phenylpropane, isopropylbenzene, n-butylbenzene, tert-butylbenzene, sec-butylbenzene, o-, m-, or p-xylene, and 2-, 3- or 4-ethyltoluene; ketones such as acetone, methyl ethyl ketone, methyl isobutyl ketone, and cyclohexanone; amides such as dimethylformamide, N,N-dimethylacetoacetamide, and H-methylpyrrolidone; nitriles such as acetonitrile; natural oils such as oleic oil, jojoba oil, olive oil, coconut oil, grapeseed oil, castor oil, rice bran oil, horse oil, and mink oil; and the like.

These dispersion media may be used singly or two or more dispersion media may be used in a mixture form.

In a case where the surface-modified zinc oxide particles are used for cosmetics, as the dispersion medium, the above chain-like polysiloxane, the above cyclic polysiloxane, the above modified polysiloxane, the above hydrocarbon oil, the above ester oil, the above higher fatty acid, the above higher alcohol, the above natural oil, ethanol, glycerin, and the like are preferably used.

These dispersion media may be used singly or two or more dispersion media may be used in a mixture form.

The liquid dispersion of the present embodiment may include a commonly-used additive as long as the characteristic thereof is not impaired.

Examples of the additive include a preservative, a dispersant, a dispersion aid, a stabilizer, a water-soluble binder, a viscosity improver, an oil-soluble chemical, oil-soluble pigments, oil-soluble proteins, an UV absorber, and the like.

The particle diameter (d50) when the cumulative volume percentage of the particle size distribution in the liquid dispersion of the present embodiment is 50% is arbitrarily selected, but is preferably 300 nm or less (0.3 μm or less), more preferably 250 nm or less, and still more preferably 200 nm or less. The particle diameter (d50) may be 150 nm or less or 100 nm or less.

The lower limit value of d50 is not particularly limited and may be, for example, 20 nm or more, may be 40 nm or more, or may be 60 nm or more.

The upper limit value and lower limit value of d50 can be arbitrarily combined together.

In addition, the particle diameter (d90) when the cumulative volume percentage of the particle size distribution in the liquid dispersion of the present embodiment is 90% is preferably 350 nm or less, more preferably 300 nm or less, and still more preferably 250 nm or less.

The lower limit value of d90 is not particularly limited and may be, for example, 60 nm or more, may be 80 nm or more, or may be 100 nm or more.

The upper limit value and lower limit value of d90 can be arbitrarily combined together.

In a case where d50 of the liquid dispersion is 300 nm or less, when a cosmetic produced using this liquid dispersion has been applied to the skin, it is easy to uniformly distribute the surface-modified zinc oxide particles and an ultraviolet shielding effect improves, which is preferable. In addition, in a case where d90 of the liquid dispersion is 350 nm or less, the transparency of the liquid dispersion is high, and the transparency of cosmetics produced using this liquid dispersion also becomes high, which is preferable.

That is, when d50 and d90 in the liquid dispersion of the present embodiment are within the above-described ranges, it is possible to obtain a liquid dispersion having excellent transparency and an excellent ultraviolet shielding property. In addition, cosmetics produced using this liquid dispersion are also excellent in terms of transparency and an ultraviolet shielding property.

Examples of a method for measuring the cumulative volume percentage of the particle size distribution in the liquid dispersion of the present embodiment include a method in which a dynamic light scattering type particle size distribution-measuring instrument (model number: LB-550, manufactured by Horiba, Ltd.) is used.

The content of the surface-modified zinc oxide particles in the liquid dispersion of the present embodiment is appropriately adjusted depending on the intended characteristics of the liquid dispersion.

In the case of using the liquid dispersion of the present embodiment in a cosmetic, the content of the surface-modified zinc oxide particles in the liquid dispersion is preferably 30% by mass or more, more preferably 40% by mass or more, and still more preferably 50% by mass or more. In addition, the content of the surface-modified zinc oxide particles in the liquid dispersion is preferably 90% by mass or less, more preferably 85% by mass or less, and still more preferably 80% by mass or less.

The upper limit value and lower limit value of the content of the surface-modified zinc oxide particles in the liquid dispersion can be arbitrarily combined together.

When the content of the surface-modified zinc oxide particles in the liquid dispersion is within the above range, the surface-modified zinc oxide particles are contained at a high concentration in the liquid dispersion. Therefore, it is possible to improve the degree of freedom in formulation of cosmetics that are produced using the liquid dispersion and to adjust the viscosity of the liquid dispersion to a range where handling is easy.

A method for producing the liquid dispersion of the present embodiment is not particularly limited. Examples thereof include a method in which the surface-modified zinc oxide particles of the present embodiment and a dispersion medium are mechanically dispersed with a well-known dispersion apparatus.

The dispersion apparatus can be selected as desired. Examples of the dispersion apparatus include a stirrer, a planetary mixer, a homogenizer, an ultrasonic homogenizer, a sand mill, a ball mill, a roll mill, and the like.

The liquid dispersion of the present embodiment can be used for, in addition to cosmetics, paints and the like having an ultraviolet shielding function, a gas transmission-suppressing function, or the like.

Since the liquid dispersion of the present embodiment contains the surface-modified zinc oxide particles of the present embodiment, the production efficiency of the liquid dispersion is favorable, and high ultraviolet shielding properties are stably exhibited.

[Composition]

A composition of the present embodiment contains the surface-modified zinc oxide particles of the present embodiment, a resin, and a dispersion medium. The composition may be prepared by preparing the surface-modified zinc oxide particles of the present embodiment and mixing the surface-modified zinc oxide particles with a resin and a dispersion medium.

The content of the surface-modified zinc oxide particles in the composition of the present embodiment is appropriately adjusted depending on the intended characteristics of the composition. The content of the surface-modified zinc oxide particles in the composition of the present embodiment is, for example, preferably 10% by mass or more and 40% by mass or less and more preferably 20% by mass or more and 30% by mass or less.

When the content of the surface-modified zinc oxide particles in the composition is within the above range, the surface-modified zinc oxide particles are contained at a high concentration in the composition. Therefore, the characteristics of the surface-modified zinc oxide particles can be sufficiently obtained, and a composition in which the surface-modified zinc oxide particles are uniformly dispersed can be obtained.

The dispersion medium is not particularly limited as long as the dispersion medium is commonly used for industrial applications. Examples of the dispersion medium include water, alcohols ouch as methanol, ethanol, and propanol, methyl acetate, ethyl acetate, toluene, methyl ethyl ketone, methyl isobutyl ketone, and the like.

The content of the dispersion medium in the composition of the present embodiment is not particularly limited and is appropriately adjusted depending on the intended characteristics of the composition.

The resin is not particularly limited as long as the resin is commonly used for industrial applications. Examples of the resin include an acrylic resin, an epoxy resin, a urethane resin, a polyester resin, a silicone resin, and the like.

The content of the resin in the composition of the present embodiment is not particularly limited and is appropriately adjusted depending on the intended characteristics of the composition.

The composition of the present embodiment may contain a commonly-used additive to an extent that the characteristics thereof are not impaired.

Examples of the additives include a polymerization initiator, a dispersant, a preservative, and the like.

A method for producing the composition of the present embodiment is not particularly limited. Examples thereof include a method in which the surface-modified zinc oxide particles of the present embodiment, a resin, and a dispersion medium are mechanically mixed with a well-known mixing apparatus.

In addition, examples thereof include a method in which the above-described liquid dispersion and the resin are mechanically mixed together using a well-known mixing apparatus.

Examples of the mixing apparatus include a stirrer, a planetary mixer, a homogenizer, an ultrasonic homogenizer, and the like.

A coated film can be formed by applying the composition of the present embodiment to a plastic base material such as a polyester film using a normal application method such as a roll coating method, a flow coating method, a spray coating method, a screen printing method, a brush coating method, or an immersion method. The coated film can be used as an ultraviolet-shielding film or a gas barrier film.

Since the composition of the present embodiment contains the surface-modified zinc oxide particles of the present embodiment, the production efficiency of the composition is favorable, and high ultraviolet shielding properties are stably exhibited.

[Cosmetic]

A cosmetic of the present embodiment contains at least one of the surface-modified zinc oxide particles of the present embodiment and the liquid dispersion of the present embodiment and a cosmetic base raw material.

Here, the cosmetic base raw material refers to various raw materials that form the main body of the cosmetic product, and examples thereof include an oily raw material, an aqueous raw material, a surfactant, a powder raw material, and the like.

Examples of the oily raw material include fats and oils, higher fatty acids, higher alcohols, ester oils, and the like.

Examples of the aqueous raw material include purified water, alcohol, a viscosity improver, and the like.

Examples of the powder raw material include a colored pigment, a white pigment, a pearl agent, an extender pigment, and the like.

In the present embodiment, as the cosmetic base raw material, an oily raw material, a powder raw material, or an oily raw material and a powder raw material can be preferably used, and an oily raw material can be more preferably used.

The cosmetic of the present embodiment may means a cosmetic where surface-modified zinc oxide particles are contained in an oil component (oil phase) in the production process or in the final form such as an oily cosmetic, an emulsion type cosmetic containing surface-modified zinc oxide particles in an oil phase, or a powdery solid cosmetic produced by mixing surface-modified zinc oxide particles and an oil, then, removing the oil and forming the surface-modified zinc oxide particles.

The emulsion type cosmetic may be an O/W type emulsion or may be a W/O type emulsion.

In other words, the cosmetic of the present embodiment preferably contains at least one of the surface-modified zinc oxide particles of the present embodiment and the liquid dispersion of the present embodiment in an oil component or an oil phase.

The oil component that is used in the oily cosmetic or the oil phase of emulsion is not particularly limited as long as the oil component is commonly used in cosmetics. Examples thereof include silicone oil, oil and fat, higher fatty acid, higher alcohol, ester oil, natural oil, and the like.

In addition, the cosmetic of the present embodiment may contain the above-described aqueous raw material, surfactant, powder raw material, and the like to an extent that the characteristics of the cosmetic are not impaired.

The cosmetic of the present embodiment can be obtained by, for example, blending the surface-modified zinc oxide particles of the present embodiment or the liquid dispersion of the present embodiment with cosmetic base raw materials such as an emulsion, a cream, a sunscreen, a foundation, a lip stick, a blush, or an eye shadow as in the related art.

In addition, the cosmetic of the present embodiment can be obtained by blending the surface-modified zinc oxide particles of the present embodiment with an oil phase to produce an O/W type or W/O type emulsion and blending the emulsion with the cosmetic base raw materials.

The content of the surface-modified zinc oxide particles in the cosmetic of the present embodiment is appropriately adjusted depending on the intended characteristics of the cosmetic. For example, the lower limit of the content of the surface-modified zinc oxide particles may be 0.01% by mass or more, may be 0.1% by mass or more, or may be 1% by mass or more. In addition, the upper limit of the content of the surface-modified zinc oxide particles may be 50% by mass or less, may be 40% by maze or less, or may be 30% by mass or less.

The upper limit value and lower limit value of the content of the surface-modified zinc oxide particles in the cosmetic can be arbitrarily combined together.

Hereinafter, as an example of the cosmetic, a sunscreen cosmetic will be specifically described.

In order to effectively shield ultraviolet rays, particularly, long wavelength ultraviolet rays (UVA) and to obtain a favorable usability with small powdery feeling and small powdery squeak, the lower limit of the content of the surface-modified zinc oxide particles in the sunscreen cosmetic is preferably 0.01% by mass or more, more preferably 0.1% by mass or more, and still more preferably 1% by mass or more. In addition, the upper limit value of the content of the surface-modified zinc oxide particles in the sunscreen cosmetic may be 50% by mass or less, may be 40% by mass or less, or may be 30% by mass or 193. The upper limit value and lower limit value of the content of the surface-modified zinc oxide particles in the sunscreen cosmetic can be arbitrarily combined together.

The sunscreen cosmetic may include a hydrophobic dispersion medium, inorganic fine particles or an inorganic pigment other than the surface-modified zinc oxide particles, a hydrophilic dispersion medium, oil and tat, a surfactant, a moisturizing agent, a viscosity improver, a pH adjuster, a nutritional supplement, an antioxidant, a perfume, and the like as necessary.

Examples of the hydrophobic dispersion medium include a hydrocarbon oil such as liquid paraffin, squalane, isoparaffin, branched chain-like light paraffin, petrolatum, or ceresin, an ester oil such as isopropyl myristate, cetyl isooctanoate, or glyceryl trioctanoate, a silicone oil such as decamethyl cyclopentasiloxane, dimethyl polysiloxane, or methyl phenyl polysiloxane, a higher fatty acid such as lauric acid, myristic acid, palmitic acid, or stearic acid, and a higher alcohol such as lauryl alcohol, cetyl alcohol, stearyl alcohol, hexyl dodecanol, or isostearyl alcohol and the like.

Examples of the inorganic fine particles or inorganic pigment other than the surface-modified particles that are contained in the cosmetic include calcium carbonate, calcium phosphate (apatite), magnesium carbonate, calcium silicate, magnesium silicate, aluminum silicate, kaolin, talc, titanium oxide, aluminum oxide, yellow oxide of iron, y-iron oxide, cobalt titanate, cobalt violet, silicon oxide, and the like.

The sunscreen cosmetic may further contain at least one organic ultraviolet absorber.

Examples of the organic ultraviolet absorber include a benzotriazole-based ultraviolet absorber, a benzoyl methane-based ultraviolet absorber, a benzoic acid-based ultraviolet absorber, an anthranilic acid-based ultraviolet absorber, a salicylic acid-based ultraviolet absorber, a cinnamic acid-based ultraviolet absorber, a silicone-based cinnamic acid ultraviolet absorber, and the like.

Examples of the benzotriazole-based ultraviolet absorber include 2,2'-hydroxy-5-methylphenylbenzotriazole, 2-(2'-hydroxy-5'-t-octylphenyl)benzotriazole, 2-(2'-hydroxy-5'-methylphenylbenzotziazole, and the like.

Examples of the benzoyl methane-based ultraviolet absorber include dibenzalazine, dianisoylmethane, 4-tert-butyl-4'-methoxydibenzoylmethane, 1-(4'-isopropylphenyl)-3-phenyl propane-1,3-dione, 5-(3,3'-dimethyl-2-norbornylidene)-3-pentane-2-one, and the like.

Examples of the benzoic acid-based ultraviolet absorber include para-aminobenzoic acid (PABA), PABA monoglycerin ester, N,N-dipropoxy PABA ethyl ester, N,N-diethoxy PABA ethyl ester, N,N-dimethyl PABA ethyl ester, N,N-dimethyl PABA butyl ester, N,N-dimethyl PABA methyl ester, and the like.

Examples of the anthranilic acid-based ultraviolet absorber include homo menthyl-N-acetyl anthranilate and the like.

Examples of the salicylic acid-based ultraviolet absorber include amyl salicylate, menthyl salicylate, homo menthyl salicylate, octyl salicylate, phenyl salicylate, benzyl salicylate, p-2-propanol phenyl salicylate, and the like.

Examples of the cinnamic acid-based ultraviolet absorber include octyl methoxycinnamate(ethylhexyl methoxycinnamate), di-para methoxy cinnamate-mono-2-glyceryl ethylhexanoate, octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxy cinnamate, isopropyl-p-methoxy cinnamate, isoamyl-p-methoxy cinnamate, octyl-p-methoxy cinnamate(2-ethylhexyl-p-methoxy cinnamate), 2-ethoxyethyl-p-methoxy cinnamate, cyclohexyl-p-methoxy cinnamate, ethyl-α-cyano-β-phenyl cinnamate, 2-ethylhexyl-α-cyano-β-phenyl cinnamate, glyceryl mono-2-ethylhexanoyl-diparamethoxy cinnamate, and the like.

Examples of the silicone-based cinnamic acid ultraviolet absorber include [3-bis(trimethylsiloxy)methylsilyl-1-methylpropyl]-3,4,5-trimethoxy cinnamate, [3-bis(trimethylsiloxy)methylsilyl-3-methylpropyl]-3,4,5-trimethoxy cinnamate, [3-bis(trimethylsiloxy)methylsilylpropyl]-3,4,5-trimethoxy cinnamate, [3-bis(trimethylsiloxy)methylsilylbutyl]-3,4,5-trimethoxy cinnamate, [3-tris(trimethylsiloxy)silylbutyl]-3,4,5-trimethoxy cinnamate, [3-tris(trimethylsiloxy)silyl-1-methylpropyl]-3,4-dimethoxy cinnamate, and the like.

Examples of the organic ultraviolet absorbers other than the above-described ultraviolet absorbers include 3-(4'-methylbenzyliene)-d,l-camphor, 3-benzylidene-d,l-camphor, urocanic acid, ethyl urocanate esters, 2-phenyl-5-methylbenzoxane, 5-(3,3'-dimethyl-2-norbornylidene)-3-pentane-2-one, silicone-denatured ultraviolet absorbers, fluorine-denatured ultraviolet absorbers, and the like.

Since the cosmetic of the present embodiment contains the surface-modified zinc oxide particles of the present embodiment and is thus easily dispersed in oil components, the production efficiency is favorable, and high ultraviolet shielding properties are stably exhibited.

EXAMPLES

Hereinafter, the present invention will be more specifically described with examples and comparative examples, but the present invention is not limited to the following examples.

Example 1

"Production of Surface-Modified Zinc Oxide Particles"

33.3 parts by mass of zinc oxide particles having a specific surface area of 21.3 $m^2/g$ and b* of 3.33 (manufactured by Sumitomo Osaka Cement Co., Ltd.), 2.0 parts by mass of octyltriethoxysilane (manufactured by Shin-Etsu Chemical Co., Ltd., trade name: KBE-3083), 0.4 parts by mass of pure water, and 64.3 parts by mass of isopropyl alcohol was mixed together.

Next, this liquid mixture was dispersed for 3 hours using a bead mill. As dispersion conditions, the rotation speed was set to 2500 rpm, and the temperature was set to 20° C.

A liquid dispersion from which beads were removed was separated into solid and liquid and dried at 80° C. for 2 hours to obtain surface-modified zinc oxide particles of Example 1.

The specific surface area of the surface-modified zinc oxide particles of Example 1 was measured using a full automatic specific surface area-measuring instrument (trade name: Macsorb HM Hodel-1201, manufactured by Mountech Co., Ltd.). The result is shown in Table 1.

In addition, d50 or b* of these particles was also measured by methods to be described below.

"Measurement of b* of Surface-Modified Zinc Oxide Particles"

b* of the surface-modified zinc oxide particles of Example 1 was measured using a spectral colorimeter (manufactured by Nippon Denshoku Industries Co., Ltd., Spectro Color Meter SE7700). As reflection (optical 2-degree visual field) measurement conditions, the measurement diameter φ was set to 10 mm, and a D65 light source was used as a light source in the measurement.

As a measurement sample, 10 g of the surface-modified zinc oxide particles of Example 1 was put into a 30 mL screw tube and tapped 30 times on a table, and the bottom surface of this screw tube was used as a measurement surface. The result is shown in Table 1.

"Production of Liquid Dispersion"

10 g of the surface-modified zinc oxide particles of Example 1, 88 g of cyclopentasiloxane (manufactured by Dow Toray Co., Ltd., model number: DOWSIL SH 245 Fluid), and 2 g of polyglyceryl-3 polydimethylsiloxyethyl dimethicone (manufactured by Shin-Etsu Chemical Co., Ltd., model number: KF-4106) were mixed to obtain a liquid mixture.

Next, a dispersion treatment was performed on this liquid mixture at 9,500 rpm for 5 minutes using a homogenizer (manufactured by IKA, ULTRA-TURRAX (registered trademark) series: T25 basic) to obtain a liquid dispersion of Example 1.

"Evaluation of Dispersibility by Particle Size Distribution"

The liquid dispersion of Example 1 was diluted with cyclopentasiloxane such that the content of the surface-modified zinc oxide particles became 0.01% by mass to produce a measurement solution.

d50 was measured using this measurement solution and a laser diffraction/scattering type particle size distribution-measuring instrument (manufactured by Horiba Ltd., model number; LA-920). The result is shown in Table 1.

In addition, the particle diameter (d10) when the cumulative volume percentage of the particle size distribution was 10% and the particle diameter (d90) when the cumulative volume percentage of the particle size distribution was 90% were measured in the same manner as d50. The result is shown in Table 1.

"Evaluation of Transparency of Liquid Diapersion"

The liquid dispersion of Example 1 was diluted with cyclopentasiloxane such that the concentration of the surface-modified zinc oxide particles became 0.005% by mass.

The linear transmittance T1 (1) of this diluted solution at 360 nm and 550 nm and the total transmittance T2 (t) at 360 nm and 550 ram were measured using an UV-visible/NIR spectrophotometer (manufactured by JASCO Corporation, Model No.: V-770). The result is shown in Table 1.

A low transmittance at 360 nm indicates that the ultraviolet shielding properties are favorable. Therefore, the transmittance at 360 nm is preferably low.

A high transmittance at 550 nm indicates that the transparency is favorable. Therefore, the transmittance at 550 nm is preferably high.

Example 2

Surface-modified zinc oxide particles of Example 2 were obtained in the same manner as in Example 1 except that, in Example 1, zinc oxide particles having a specific surface area of 24.2 $m^2/g$ and b* of 3.60 were used instead of the use of the zinc oxide particles having a specific surface area of 21.3 $m^2/g$ and b* of 3.33.

The specific surface area and b* were measured in the same manner as in Example 1. The results are shown in Table 1.

A liquid dispersion of Example 2 was obtained in the same manner as in Example 1 except that the surface-modified zinc oxide particles of Example 2 were used instead of the use of the surface-modified zinc oxide particles of Example 1.

d10, d50, d90, T1, and T2 were measured in the same manner as in Example 1. The results are shown in Table 1.

Example 3

Surface-modified zinc oxide particles of Example 3 were obtained in the same manner as in Example 1 except that, in Example 1, zinc oxide particles having a specific surface area of 38.2 $m^2/g$ and b* of 3.42 were used instead of the use of the zinc oxide particles having a specific surface area of 21.3 $m^2/g$ and b* of 3.33.

The specific surface area and b* were measured in the same manner as in Example 1. The results are shown in Table 1.

A liquid dispersion of Example 3 was obtained in the same manner as in Example 1 except that the surface-modified zinc oxide particles of Example 3 were used instead of the use of the surface-modified zinc oxide particles of Example 1.

d10, d50, d90, T1, and T2 were measured in the same manner as in Example 1. The results are shown in Table 1.

Example 4

Surface-modified zinc oxide particles of Example 4 were obtained in the same manner as in Example 3 except that, in Example 3, a dispersion treatment was performed for 9 hours instead of performing the dispersion treatment for 3 hours.

The product (impulse) of the centrifugal force and the dispersion time during dispersion was about three times that of Example 1. The specific surface area and b* were measured in the same manner as in Example 1. The results are shown in Table 1.

A liquid dispersion of Example 4 was obtained in the same manner as in Example 1 except that the surface-modified zinc oxide particles of Example 4 were used instead of the use of the surface-modified zinc oxide particles of Example 1.

d10, d50, d90, T1, and T2 were measured in the same manner as in Example 1. The results are shown in Table 1.

Comparative Example 1

Surface-modified zinc oxide particles of Comparative Example 1 were obtained in the same manner as in Example 3 except that, in Example 3, a dispersion treatment was performed for 5 minutes instead of performing the dispersion treatment for 3 hours.

The product (impulse) of the centrifugal force and the dispersion time during dispersion was about 1/40 times that of Example 1. The specific surface area and b* were measured in the same manner as in Example 1. The results are shown in Table 1.

A liquid dispersion of Comparative Example 1 was obtained in the same manner as in Example 1 except that the surface-modified zinc oxide particles of Comparative Example 1 were used instead of the use of the surface-modified zinc oxide particles of Example 1.

d10, d50, d90, T1, and T2 were measured in the same manner as in Example 1. The results are shown in Table 1.

Comparative Example 2

100 parts by mass of zinc oxide particles having a specific surface area of 38.2 $m^2/g$ and b* of 3.42 were injected into a Henschel mixer. While the zinc oxide particles were stirred with a Henschel mixer, a liquid mixture of 5 parts by mass of octyltriethoxysilane (trade name: KBE-3083, manufactured by Shin-Etsu Chemical Co., Ltd.), 0.375 parts by mass of pure water, and 7.125 parts by mass of isopropyl alcohol was added thereto. The mixture was mixed in the Henschel mixer and stirred for 1 hour.

Next, the obtained mixture was pulverized with a jet mill, and the pulverized powder was dried at 100° C. to obtain surface-modified zinc oxide particles of Comparative Example 2.

The specific surface area and b* were measured in the same manner as in Example 1. The results are shown in Table 1.

A liquid dispersion of Comparative Example 2 was obtained in the same manner as in Example 1 except that the surface-modified zinc oxide particles of Comparative Example 2 were used instead of the use of the surface-modified zinc oxide particles of Example 1.

d10, d50, d90, T1, and T2 were measured in the same manner as in Example 1. The results are shown in Table 1.

TABLE 1

| | Specific surface area | Chromaticity | Particle size distribution [μm] | | | T1 (linear transmission) [%] | | T2 (total transmission) [%] | |
|---|---|---|---|---|---|---|---|---|---|
| | [$m^2$/g] | b* | d10 | d50 | d90 | 360 nm | 550 nm | 360 nm | 550 nm |
| Example 1 | 20.7 | 5.90 | 0.18 | 0.28 | 0.42 | 22.4 | 85.3 | 28.5 | 94.7 |
| Example 2 | 24.8 | 4.77 | 0.14 | 0.20 | 0.31 | 23.7 | 90.4 | 30.7 | 94.8 |
| Example 3 | 40.5 | 5.29 | 0.13 | 0.19 | 0.26 | 24.2 | 91.9 | 30.8 | 96.2 |
| Example 4 | 43.6 | 9.34 | 0.13 | 0.18 | 0.26 | 25.1 | 93.8 | 32.2 | 97.0 |
| Comparative Example 1 | 40.1 | 3.02 | 1.12 | 4.95 | 8.59 | 38.7 | 88.6 | 40.8 | 97.1 |
| Comparative Example 2 | 37.8 | 3.75 | 2.94 | 9.86 | 16.8 | 48.7 | 73.9 | 56.2 | 87.6 |

From the results of Table 1, it was confirmed that the surface-modified zinc oxide particles of Example 1 to Example 4 had small d50 and excellent ultraviolet shielding properties compared with those of the surface-modified zinc oxide particles of Comparative Example 1 and Comparative Example 2 and had transparency equal to or higher than that of the surface-modified zinc oxide particles of Comparative Example 1 and Comparative Example 2.

Example 5

Surface-modified zinc oxide particles of Example 5 were obtained in the same manner as in Example 1 except that, in Example 1, zinc oxide particles having a specific surface area of 5.1 $m^2/g$ and b* of 2.51 were used instead of the use of the zinc oxide particles having a specific surface area of 21.3 $m^2/g$ and b* of 3.33.

The specific surface area and b* were measured in the same manner as in Example 1. The results are shown in Table 2.

A liquid dispersion of Example 5 was obtained in the same manner as in Example 1 except that the surface-modified zinc oxide particles of Example 5 were used instead of the use of the surface-modified zinc oxide particles of Example 1.

d10, d50, and d90 were measured in the same manner as in Example 1. The results are shown in Table 2.

Example 6

Surface-modified zinc oxide particles of Example 6 were obtained in the same manner as in Example 1 except that, in Example 1, zinc oxide particles having a specific surface area of 7.4 $m^2/g$ and b* of 7.98 were used instead of the use of the zinc oxide particles having a specific surface area of 21.3 $m^2/g$ and b* of 3.33.

The specific surface area and b were measured in the same manner as in Example 1. The results are shown in Table 2.

A liquid dispersion of Example 6 was obtained in the same manner as in Example 1 except that the surface-modified zinc oxide particles of Example 6 were used instead of the use of the surface-modified zinc oxide particles of Example 1.

d10, d50, and d90 were measured in the same manner as in Example 1. The results are shown in Table 2.

Comparative Example 3

Surface-modified zinc oxide particles of Comparative Example 3 were obtained in the same manner as in Example 5 except that, in Example 5, a dispersion treatment was performed for 5 minutes instead of performing the dispersion treatment for 3 hours.

The product (impulse) of the centrifugal force and the dispersion time during dispersion was about 1/40 times that of Example 1. The specific surface area and b* were measured in the same manner as in Example 1. The results are shown in Table 2.

A liquid dispersion of Comparative Example 0.3 was obtained in the same manner as in Example 1 except that the surface-modified zinc oxide particles of Comparative Example 3 were used instead of the use of the surface-modified zinc oxide particles of Example 1.

d10, d50, and d90 were measured in the same manner as in Example 1. The results are shown in Table 2.

TABLE 2

| | Specific surface area | Chromaticity | Particle size distribution [μm] | | |
|---|---|---|---|---|---|
| | [m$^2$/g] | b* | d10 | d50 | d90 |
| Example 5 | 4.7 | 8.5 | 0.30 | 0.48 | 0.83 |
| Example 6 | 7.5 | 14.2 | 0.14 | 0.21 | 0.30 |
| Comparative Example 3 | 5.0 | 5.8 | 0.29 | 3.54 | 9.84 |

It was confirmed that the surface-modified zinc oxide particles of Example 5 and Example 6 had a smaller d50 than the surface-modified zinc oxide particles of Comparative Example 3. In addition, it was confirmed that the surface-modified zinc oxide particles of Example 5 and Example 6 are superior to Comparative Example 3 in ultraviolet shielding properties and have transparency equal to or higher than that of Comparative Example 3.

"Evaluation of Easy Dispersibility"

1 g of the surface-modified zinc oxide particles of each of Example 1 to Example 6 and Comparative Example 1 to Comparative Example 3 were gently added to a screw tube containing 20 g of cyclopentasiloxane, and the state of the screw tube after 20 minutes was observed.

As a result, it was confirmed that, in Example 1 to Example 6, the surface-modified zinc oxide particles were dispersed throughout; however, in the surface-modified zinc oxide particles of Comparative Example 1 to Comparative Example 3, many particles settled. The results of Example 4 and Comparative Example 2 are shown in FIG. 1. The screw tube on the right side of FIG. 1 contains the surface-modified zinc oxide particles obtained in Example 4, and the screw tube on the left side of FIG. 1 contains the surface-modified zinc oxide particles obtained in Comparative Example 2. As shown in FIG. 1, it was confirmed that, in Example 4, the surface-modified zinc oxide particles were dispersed throughout. On the other hand, in Comparative Example 2, it was confirmed that many surface-modified zinc oxide particles settled.

That is, it was found that the surface-modified zinc oxide particles of Example 1 to Example 6, for which d50 of a liquid dispersion produced under predetermined conditions became 4 μm or less, were easily dispersed in the dispersion medium even with a small amount of dispersion energy at the time of producing cosmetics.

INDUSTRIAL APPLICABILITY

The present invention is capable of providing surface-modified zinc oxide particles that are easily blended with oily cosmetics and are excellent in terms of transparency and ultraviolet shielding properties. Since the surface-modified zinc oxide particles of the present invention is excellent in terms of dispersibility and thus have excellent ultraviolet shielding properties and also transparency equal to or higher than that of conventional particles, the surface-modified zinc oxide particles are highly valuable industrially in the case of being used in cosmetics.

The invention claimed is:

1. Surface-modified zinc oxide particles, wherein the surface-modified zinc oxide particles have a silane coupling agent having an alkoxy group on surfaces thereof, and a particle diameter d50 thereof is 4 μm or less, wherein the particle diameter d50 reflects a dispersion state of the surface-modified zinc oxide particles, including a degree of agglomeration thereof, in a measurement solution, wherein the particle diameter d50 represents a particle diameter at which a cumulative volume percentage of a particle size distribution of the surface-modified zinc oxide particles in the measurement solution is 50%, wherein the particle diameter d50 is obtained when the surface-modified zinc oxide particles are measured with a laser diffraction/scattering type particle size distribution-measuring instrument by following a measurement method wherein the measurement method includes the following:

10 g of the surface-modified zinc oxide particles, 88 g of cyclopentasiloxane, and 2 g of polyglyceryl-3 polydimethylsiloxyethyl dimethicone are mixed to obtain a liquid mixture, a dispersion treatment is performed on the liquid mixture at 9,500 rpm for 5 minutes using a homogenizer to obtain a liquid dispersion, the liquid dispersion is diluted with cyclopentasiloxane so that a content of the surface-modified zinc oxide particles in the liquid dispersion is 0.01% by mass to produce the measurement solution, and the particle diameter d50 is measured with the laser diffraction/scattering type particle size distribution-measuring instrument using the measurement solution.

2. The surface-modified zinc oxide particles according to claim 1, wherein b* in an L*a*b* colorimetric system chromaticity diagram thereof is 4.0 or more and 18 or less.

3. The surface-modified zinc oxide particles according to claim 1, wherein the silane coupling agent is at least one selected from a group consisting of an alkylalkoxysilane, an allylalkoxysilane, a polysiloxane having an alkyl group in a side chain, and a polysiloxane having an allyl group in a side chain.

4. The surface-modified zinc oxide particles according to claim 1, wherein the silane coupling agent is at least one selected from a group consisting of octyltriethoxysilane, octyltrimethoxysilane, and a dimethoxydiphenylsilane-triethoxycaprylylsilane crosspolymer.

5. The surface-modified zinc oxide particles according to claim 1, wherein the surface-modified zinc oxide particles are obtained by preparing a liquid mixture containing 1% by mass or more and 55% by mass or less of zinc oxide particles, 40% by mass or more and 95% by mass or less of a solvent, and a silane coupling agent having an alkoxy group, dispersing the liquid mixture until b* of surface-modified zinc oxide particles thereof becomes 4.0 or more and 18 or less, and then drying the liquid mixture.

6. The surface-modified zinc oxide particles according to claim 5, wherein the liquid mixture further contains water and a catalyst.

7. The surface-modified zinc oxide particles according to claim 1, wherein the particle diameter d50 represents a particle diameter d50 of agglomeration of the surface-modified zinc oxide particles included in the measurement solution.

8. The surface-modified zinc oxide particles according to claim 1, wherein the particle diameter d50 thereof is 2.00 μm or less.

9. The surface-modified zinc oxide particles according to claim 1, wherein the particle diameter d50 thereof is 1.00 μm or less.

10. The surface-modified zinc oxide particles according to claim 1, wherein the surface-modified zinc oxide particles have a specific surface area of 1.5 $m^2/g$ or more and 55 $m^2/g$ or less.

11. The surface-modified zinc oxide particles according to claim 1, wherein the surface-modified zinc oxide particles have a specific surface area of 8 $m^2/g$ or more and 50 $m^2/g$ or less.

12. The surface-modified zinc oxide particles according to claim 1, wherein the surface-modified zinc oxide particles have a specific surface area of 20 $m^2/g$ or more and 50 $m^2/g$ or less.

13. The surface-modified zinc oxide particles according to claim 1, wherein the surface-modified zinc oxide particles are dried surface-modified zinc oxide particles.

14. The surface-modified zinc oxide particles according to claim 1, wherein a primary particle diameter of the surface-modified zinc oxide particles is from 21 nm to 713 nm.

15. A liquid dispersion comprising:

the surface-modified zinc oxide particles according to claim 1; and a dispersion medium.

16. A cosmetic comprising:

the surface-modified zinc oxide particles according to claim 1; and a cosmetic base raw material.

17. A method for selecting the surface-modified zinc oxide particles according to claim 1, comprising:

preparing surface-modified zinc oxide particles having a silane coupling agent having an alkoxy group on surfaces thereof, mixing 10 g of the surface-modified zinc oxide particles, 88 g of cyclopentasiloxane, and 2 g of polyglyceryl-3 polydimethylsiloxyethyl dimethicone to obtain a liquid mixture, performing a dispersion treatment on the obtained liquid mixture at 9,500 rpm for 5 minutes using a homogenizer to obtain a liquid dispersion, producing a measurement solution by diluting the liquid dispersion with cyclopentasiloxane so that a content of the surface-modified zinc oxide particles in the liquid dispersion is 0.01% by mass, measuring a particle diameter d50, which is obtained when a cumulative volume percentage of a particle size distribution thereof is 50%, with a laser diffraction/scattering type particle size distribution-measuring instrument using the measurement solution, determining whether or not the d50 is 4 μm or less, and selecting the surface-modified zinc oxide particles in a case where the d50 is 4 μm or less.

18. A method for producing the surface-modified zinc oxide particles according to claim 1, comprising:

a step of putting a silane coupling agent having an alkoxy group, a solvent, and zinc oxide particles into a disperser to produce a liquid mixture; and a step of dispersing the liquid mixture with the disperser to obtain surface-modified zinc oxide particles of which d50 thereof is 4 μm or less, wherein, in the step wherein the liquid mixture is produced, a solvent content in the liquid mixture is 40% by mass or more and 95% by mass or less.

19. The method for producing the surface-modified zinc oxide particles according to claim 18, wherein the d50 represents a particle diameter d50 of agglomeration of the surface-modified zinc oxide particles.

20. The method for producing the surface-modified zinc oxide particles according to claim 18, further comprising a step of drying the surface-modified zinc oxide particles, after the step of dispersing the liquid mixture with the disperser.

* * * * *